United States Patent [19]
Beard et al.

[11] 3,935,209
[45] Jan. 27, 1976

[54] 5(6)-BENZENE RING SUBSTITUTED BENZIMIDAZOLE-2-CARBAMATE DERIVATIVES HAVING ANTHELMINTIC ACTIVITY

[75] Inventors: Colin C. Beard, Palo Alto; John A. Edwards, Los Altos; John H. Fried, Palo Alto, all of Calif.

[73] Assignee: Syntex (U.S.A.) Inc., Palo Alto, Calif.

[22] Filed: Feb. 11, 1974

[21] Appl. No.: 441,222

Related U.S. Application Data

[63] Continuation-in-part of Ser. No. 340,581, March 12, 1973, abandoned.

[52] U.S. Cl. .................... 260/250 BN; 260/250 A; 260/256.4 C; 260/256.5 R; 260/294.8 C; 260/295 F; 260/302 H; 260/304; 260/307 R; 260/307 H; 260/308 R; 260/308 D; 260/309.2; 260/310 R; 260/999
[51] Int. Cl.[2] ....................... C07D 235/32
[58] Field of Search ..... 260/302 H, 294.8 C, 295 F, 260/309.2, 256.5 R, 256.4 C, 250 BN, 250 A, 308 R, 307 R, 307 H, 310 R

[56] References Cited
UNITED STATES PATENTS
3,401,173  9/1968  Chow et al. ............... 260/302 H
3,839,347  10/1974  Fisher et al. .............. 260/302 H Primary Examiner—R. Gallagher
Attorney, Agent, or Firm—Joseph I. Hirsch; William B. Walker

[57] ABSTRACT

Benzene ring substituted benzimidazole-2-carbamate derivatives represented by the formula:

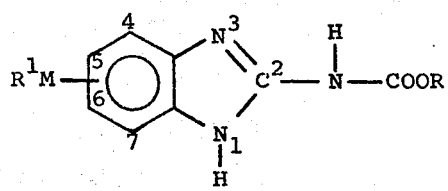

where R is a lower alkyl group having 1 to 4 carbon atoms; $R^1$ is a heterocyclic ring having 1–4 hetero atoms; and M is O, S, or $$\overset{S}{\underset{O}{\uparrow}}$$

The $R^1M$-substitution is at the 5(6)-position.
The compounds are useful as pesticides, particularly as anthelmintic and antifungal agents.

22 Claims, No Drawings

5(6)-BENZENE RING SUBSTITUTED BENZIMIDAZOLE-2-CARBAMATE DERIVATIVES HAVING ANTHELMINTIC ACTIVITY

FIELD OF THE INVENTION

This invention relates to novel chemical compounds. More particularly, this invention relates to novel anthelmintically active benzimidazole-2-carbamate derivatives wherein the benzene ring is substituted at the 5(6)-position.

BACKGROUND OF THE INVENTION

Anthelmintically active benzimidazole-2-carbamate derivatives either unsubstituted at the 5(6)-position or substituted with different substituents than those described and claimed herein are known in this art (for example, see U.S. Letters Patent Nos. 3,480,642; 3,573,321; 3,574,845; 3,578,676; and 3,595,870). Related fungicidal compounds are also shown in U.S. Letters Patent Nos. 2,933,504 and 3,010,968.

SUMMARY OF THE INVENTION

The novel benzene ring substituted benzimidazole-2-carbamate derivatives of the present invention can be represented by the following formula:

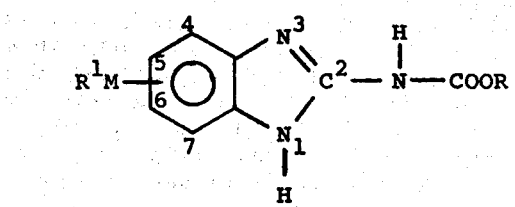

where R is a lower alkyl group having 1 to 4 carbon atoms; $R^1$ is a heterocyclic ring having 1–4 hetero atoms; and M is O, S, or

The $R^1M$-substitution is at the 5(6)-position.

The hydrogen on the nitrogen at the 1-position can be replaced with substituents which do not adversely affect the anthelmintic and/or antifungal properties of the basic compound, including N-alkylcarbamoyl, N,N-dialkylcarbamoyl, N-alkoxycarbonylcarbamoyl, cyano, trichloromethylthio, alkylthio, phenylthio, nitrophenylthio, alkylsulfinyl, phenylsulfinyl, acyl, alkoxycarbonyl, benzoyl, alkoxycarbonylalkylcarbonyl, alkyl, alkenyl, benzyl, alkoxyalkyl, alkoxycarbonylalkyl, carboxyalkyl, hydroxy, and conventional esters and ethers thereof, etc.

As used in this specification and claims, the term "lower alkyl" refers to both straight and branched chain alkyl groups having a total of from 1 through 4 carbon atoms, and thus includes methyl, ethyl, n-propyl, isopropyl, n-butyl, isobutyl, and t-butyl. The term "heterocyclic ring" refers to both unsubstituted and substituted heterocyclic rings containing 1–4 hetero atoms and includes both saturated and unsaturated heterocyclic rings. Typical heterocyclic rings expressed in radical form include, for example, thiazolyl; pyridyl; imidazolyl; pyrimidyl; thienyl; pyridazinyl; pyrazinyl; pyrrolyl; pyrazolyl; oxazolyl; furyl; isothiazolyl; isoxazolyl; thiadiazolyl; triazolyl; and the like.

The compounds of the present invention, and non-toxic salts thereof formed with pharmaceutically acceptable inorganic or organic acids, possess broad spectrum activity against parasites of mammals, including both mature and immature parasitic forms, as represented for example, by the genera Trichostronglylus, Haemonchus, Ostertagia, Cooperia, Nematodirus, and Stronglyoides, and specifically, for example, against *Nematospiroides dubius*, *Hymenolepis Nana*, *Syphacia obvelata*, and/or *Aspiculuris tetraptera*. In particular, these compounds are found to exhibit high activity against various helminthic infections of the intestinal tract of economically important animals, coupled with lower systemic toxicity to the host animal.

The compounds of the present invention are also useful as antifungal agents, particularly as systemic fungicides for controlling fungal diseases of plants of economic importance.

In addition to the stated anthelminthic and anti-fungal properties, certain compounds of the present invention are also useful as intermediates in the preparation of further compounds of this invention. For example, the 5(6)-thio compounds can be prepared and then utilized as starting materials for the preparation of the corresponding 5(6)-sulfinyl compounds.

Where the compound has a basic moiety, the term non-toxic salts as used herein refers to those pharmaceutically acceptable salts of the compounds of this invention which do not adversely affect the antifungal or anthelmintic properties of the basic compound, such as those salts conventionally used in the art. Such non-toxic salts include, for example, salts of inorganic acids such as, for example, sulfuric, sulfonic, sulfamic, nitric, phosphoric, hydrochloric acids and the like, and salts of organic acids such as, for example, acetic, citric, lactic, palmitic, tartaric, succinic, maleic, benzoic acids and the like.

The amount of the compound to be administered will depend upon the actual compound utilized, and upon the weight of the animal being treated. In general, however, the daily dosage level will usually be between about 5 mg/kg and 100 mg/kg of body weight of the animal being treated. The active ingredient is adapted to be administered to the animal by mixing it with the diet of the animal, as with a feed mix, or formulating it with a non-toxic carrier to give anthelminthic compositions. The carrier may be an orally ingestible container for the active ingredient such as, for example, a gelatin capsule, or it may be an excipient of the kind normally used in medicaments of this character, including maize starch, terra alba, lactose, sucrose, calcium phosphate, gelatin, stearic acid, agar, pectin or the like. Examples of suitable liquid carriers are peanut oil, sesame oil and water.

A wide variety of pharmaceutical forms can be employed in those cases wherein the medicament is not admixed with the feed. Thus, if a solid carrier is used, the compound can be administered in tablet or capsule form. If a liquid carrier is used, the medicament may be in the form of a soft gelatin capsule or in a liquid suspension.

In general, the 5(6)-thio, and -sulfinyl compounds of the present invention can be prepared from benzene starting compounds having nitro and amino or acylamino (for example, acetamido) substituents at adjacent positions on the benzene nucleus (eg, the 1- and 2-positions), and the desired R¹M- moiety (or a moiety which can be reacted to give the desired R¹M moiety) at the 4- or 5-position of the benzene nucleus (i.e., at what will be the 5- or 6-position of the benzimidazole compound to be prepared). If the starting material has the desired R¹M moiety, the nitro group is reduced to an amino group to afford a benzene derivative having amino groups at the 1- and 2-positions. The diamino compound is then reacted with a 1,3-bis(alkoxy-carbonyl)-S-alkyl-isothiourea to give the corresponding 5(6)-substituted benzimidazole 2-carbamate derivative.

The functional moiety at the 4- or 5-position of the benzene starting material can be, for example, the thiocyanato group which can be converted to a heterocyclicthio group, which, in turn, can be converted, by known reactions, to the heterocyclicsulfinyl group. The functional moiety at the 4- or 5-position can also be chloro which can be reacted with a substituted or unsubstituted heterocyclic mercaptan to afford the corresponding heterocyclicthio compound. As above, the heterocyclicsulfinyl compounds can be prepared from the corresponding heterocyclicthio compound.

The heterocyclicoxy compounds are prepared by reacting a suitable starting material having a hydroxy group at the 4- or 5-position with a heterocyclic halide, then converting the resultant compound to the corresponding 1,2-diamino-4(5)-heterocyclicoxybenzene compound, and reacting the latter compound with a 1,3-bis(alkoxy-carbonyl)-S-alkyl-isothiourea to give the corresponding 5(6)-heterocyclicoxy-benzimidazole 2-carbamate derivative.

A suitable starting material is 1-acetamido-2-nitro-4-thiocyanatobenzene which can be prepared according to the method of F. Challenger and A. T. Peters, J. Chem. Soc., 1364 (1928). Other suitable starting materials include, for example, 1-amino-2-nitro-4-thiocyanatobenzene, 2-amino-4-chloro-1-nitrobenzene, 2-acetamido-4-chloro-1-nitrobenzene, 1-acetamido-4-hydroxy-2-nitrobenzene, 1-amino-4-hydroxy-2-nitrobenzene, and 2-amino-4-mercapto-1-nitrobenzene.

Conversion of the thiocyanato group of the 1-acetamido-2-nitro-4-thiocyanatobenzene starting material to a heterocyclicthio substituent can be effected by treatment of the aforementioned 4-thiocyanatobenzene starting material, at room temperature, with sodium borohydride in dimethylformamide for about ¼ hour to about 2 hours, followed by treatment with an activated heterocyclichalide such as, 2-bromothiazole, 2-bromopyridine, 4-bromopyridine, 2-chloropyrazine, and the like, in dimethylformamide, dimethylacetamide, quinoline, pyridine, or an alcoholic medium, such as methanol or ethanol, in the presence of base, such as potassium hydroxide, sodium hydroxide, potassium carbonate, or sodium carbonate. This latter reaction is conducted at a temperatuare from about 10° to about 150°C, generally at room temperature if feasible, for about ½ to 12 hours using an excess of the halide reactant. The reaction is preferably conducted in dimethylformamide.

Conversion of an acylamino group, for example, an acetamido group, to an amido group can be effected by treating the acylamino group-containing compound with a strong acid, such as hydrochloric acid, or strong base, such as sodium hydroxide, potassium hydroxide, potassium carbonate, or sodium carbonate in aqueous methanol at about 20°C to about 100°C for about ¼ hour to about 24 hours. The selection of either the strong acid or the strong base will depend upon the substituent at the 4- or 5-position of the benzene nucleus. Generally, for substituents disclosed a strong base is utilized; however, the necessary material for a particular substituent or compound can be determined by routine experimentation or will be apparent from the nature and chemical stability of the particular compound involved.

Reduction of the nitro group to an amino group can be effected by a variety of techniques. For example, a nitro-containing compound can be treated with iron powder and a ferrous salt, such as ferrous sulfate or ferrous chloride, in aqueous methanol at reflux under neutral conditions for about 1 to about 6 hours. Other suitable reaction media include acetic acid or concentrated hydrochloric acid, and the other suitable metals, such as zinc. It is desirable to add the iron powder in distinct portions (as opposed to all at one time), and to carefully monitor the reactants and reaction conditions to insure, for example, that sulfinyl compounds are not reduced to the corresponding thio compounds. This technique is suitable for starting materials which contain a heterocyclicthio, a heterocyclicsulfonyl, or a heterocyclicoxy substituent.

A reduction technique which is frequently suitable for use with heterocyclicthio or heterocyclicoxy substituted compounds is to treat such compounds with stannous chloride in concentrated hydrochloric acid at a temperature in a range from about −20°C to about 100°C, generally about room temperature, for about ½ to about 6 hours. An excess of the stannous chloride reactant should be utilized, generally about 5 parts (by weight) per unit weight of the starting compound.

Reduction of the nitro group to an amino group can also be effected catalytically utilizing hydrogen over a palladium/charcoal catalyst. This reaction is conducted in an inert solvent, such as methanol, at a temperature from about 0° to 35°C, generally about room temperature, for about ½ to about 2 hours. Other suitable inert solvents include ethyl acetate, acetic acid, and ethanol. This technique is particularly suitable for compounds which contain a heterocyclicoxy substituent at the 4- or 5-position of the benzene nucleus.

The reduction can also be conducted using sodium dithionite (sodium hydrosulfite) in basic aqueous methanol at reflux for 10 minutes - 6 hours.

The diamino compounds resulting from reduction of the nitro group in the starting compound to an amino group, and, if necessary, conversion of the acylamino group to an amino group, are converted to the corresponding benzimidazole 2-carbamate compounds by reacting the diamino compound with a 1,3-bis(alkoxy-carbonyl)-S-alkyl-isothiourea, for example, 1,3-bis(-methoxycarbonyl)-S-methylisothiourea or 1,3-bis(ethoxycarbonyl)-S-methyl-isothiourea, in an aqueous alcoholic medium, for example, aqueous methanol or aqueous ethanol, at from about room temperature to the reflux temperature of the reaction medium for about ½ to about 6 hours. The reaction medium is preferably made acidic to a pH of about 4–6 with, for example, a sufficient amount (e.g., 1–2 moles) of acetic acid. About 1–2 moles, generally about 1.1 moles, of the isothiourea reactant are utilized per mole of the diamino compound.

At this point there generally will be prepared a 5(6)-heterocyclicthio-benzimidazole-2-carbamate compound of the present invention. Or, as to be described below, a 5(6)-heterocyclicoxy-benzimidazole-2-carbamate will be prepared. The 5(6)-heterocyclicthio compounds can be converted, by reactions described in the next paragraph, to the corresponding 5(6)-heterocyclicsulfinyl derivatives.

Conversion of the heterocyclicthio group to the corresponding heterocyclicsulfinyl group is conveniently effected by treatment with a peracid, such as peracetic acid, perbenzoic acid, metachloroperbenzoic acid, or perphthalic acid, in an inert solvent for the compound being treated. Suitable solvent materials include, for example, methylene chloride or chloroform. If the compound being treated is not soluble in the particular reaction media desired to be utilized, then a co-solvent material, such as acetic acid or methanol, should be utilized in an amount sufficient to dissolve the compound being treated. Typically, the reaction is conducted at a temperature from about −30°C. to about room temperature for about ½ hour to about 6 hours. When it is desired to convert the heterocyclicthio group to the corresponding heterocyclicsulfinyl group, molar quantities are utilized, and reaction conditions are carefully monitored to insure that the reaction does not proceed further than desired. Optionally, such conversions can also be effected by treatment with periodate in aqueous methanol or aqueous acetonitrile at a temperature in the range of about −20°C. to about 50°C., for about ½ to about 12 hours.

When 2-amino-4-chloro-1-nitrobenzene or 2-acetamido-4-chloro-1-nitrobenzene is utilized as a starting material, it can be converted to the corresponding heterocyclicthio compound, by the reaction thereof with an appropriate heterocyclic mercaptan, such as 2-mercaptopyrimidine, 2-mercaptothiophene, 2-mercaptoimidazole, 3-mercapto-1,2,4-triazole, 2-mercapto-1-methylimidazole, and the like, in an inert solvent, such as dimethylformamide, ethanol, or methanol, in the presence of a suitable inorganic base, such as potassium hydroxide, potassium carbonate, sodium carbonate, sodium hydroxide or sodium hydride. Typically, this reaction is conducted at a temperature from about 20° to about 150°C. (i.e., to about the reflux temperature of the solvent material) for about ½ to about 6 hours, using a slight excess (1.5–2 moles) of the mercaptan reactant. If 2-acetamido-4-chloro-1-nitrobenzene is utilized as the starting material, the acetamido group can be converted to an amino group as described above. With either case, the nitro group is reduced to an amino group. The resultant 1,2-diamino compound is treated, as described above, to give the corresponding 5(6)-heterocyclicthio-, and/or 5(6)-heterocyclicsulfinyl-benzimidazole-2-carbamate compounds of this invention.

When 1-acetamido-4-hydroxy-2-nitrobenzene or 1-amino-4-hydroxy-2-nitrobenzene is utilized as the starting material, it can be reacted with a heterocyclic halide, under the conditions as set forth above, to afford the corresponding 1-acetamido (or 1-amino)-4-heterocyclicoxy-2-nitrobenzene derivative. When the 1-amino starting material is utilized, the nitro group thereon is reduced to an amino group to give the corresponding 1,2-diamino compound. When the 1-acetamido starting material is utilized, the acetamido group is converted to an amino group and the nitro group is reduced to amino group to give the corresponding 1,2-diamino compound. The 1,2-diamino compound is then reacted with a 1,3-bis(alkoxycarbonyl)-S-alkyl isothiourea, as described above, to give the corresponding 5(6)-heterocyclicoxy-benzimidazole-2-carbamate compound of the present invention.

In each of the process steps, described herein above and below, unless otherwise indicated, the respective intermediate products are preferably separated from the reaction mixture and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. Particular reaction step or steps may be conducted in a different order from that specified above since, in many instances, the particular sequence of steps is not critical. For example, the acetamido group on a 1-acetamido-4-heterocyclicoxy-2-nitrobenzene compound can be first converted to an amino group before the nitro group is reduced. Or, the nitro group can be reduced and then the acetamido group converted to the amino group to give the corresponding 1,2-diamino compound. The heterocyclicthio substituent of a 1-acetamido-4-heterocyclicthio-2-nitrobenzene compound can be converted to a heterocyclisulfinyl group prior to conversion of the acetamido and nitro groups to the corresponding amino groups. Additionally, the acetamido group of a 1-acetamido-2-nitro-4-thiocyanatobenzene can be converted to an amino group before the reaction of such compound with a heterocyclic halide or the starting material can be reacted with the heterocyclic halide and then the acetamido group converted to the corresponding amino group. In view of this disclosure, the preparation of particular compounds, including compounds falling within the scope of the present invention but not particularly described in the specification, and the various sequences of reaction steps which can be utilized to prepare such compounds, will be apparent to those skilled in this art.

Exemplary of the compounds of the present invention, as represented by the structural formula above, are the following illustrative compounds:

5(6)-(thiazol-2-ylthio)-2-carbomethoxyaminobenzimidazole;

5(6)-(thiazol-2-ylsulfinyl)-2-carbomethoxyaminobenzimidazole;

5(6)-(thiazol-2-yloxy)-2-carbomethoxyaminobenzimidazole;

5(6)-(pyrid-2-ylthio)-2-carbomethoxyaminobenzimidazole;

5(6)-(pyrid-2-ylsulfinyl)-2-carbomethoxyaminobenzimidazole;

5(6)-(pyrid-2-yloxy)-2-carbomethoxyaminobenzimidazole;

5(6)-(pyrimidin-2-ylthio)-2-carbomethoxyaminobenzimidazole;

5(6)-(pyrimidin-2-ylsulfinyl)-2-carbomethoxyaminobenzimidazole;

5(6)-(thien-2-ylthio)-2-carbomethoxyaminobenzimidazole;

5(6)-(thien-2-ylsulfinyl)-2-carbomethoxyaminobenzimidazole;
5(6)-(imidazol-2-ylthio)-carbomethoxyaminobenzimidazole;
5(6)-(imidazol-2-ylsulfinyl)-carbomethoxyaminobenzimidazole;
5(6)-(1-methylimidazol-2-ylthio)-2-carbomethoxyaminobenzimidazole;
5(6)-(1-methyl-imidazol-2-ylsulfinyl)-2-carbomethoxyaminobenzimidazole
5(6)-(pyrid-4-ylthio)-2-carbomethoxyaminobenzimidazole;
5(6)-(pyrid-4-ylsulfinyl)-2-carbomethoxyaminobenzimidazole;
5(6)-(pyrazin-2-ylthio)-2-carbomethoxyaminobenaimidazole;
5(6)-(1,2,4-triazol-3-ylthio)-2-carbomethoxyaminobenzimidazole; and
5(6)-(1,2,4-triazol-3-ylsulfinyl)-2-carbomethoxyaminobenzimidazole.

Of these compounds, the following are presently preferred since they have shown substantial activity against the helminths specifically referred to above:

5(6)-(thiazol-2-ylthio)-2-carbomethoxyaminobenzimidazole;
5(6)-(pyrid-2-ylthio)-2-carbomethoxyaminobenzimidazole;
5(6)-(pyrid-2-ylsulfinyl)-2-carbomethoxyaminobenzimidazole;
5(6)-pyrid-2-yloxy)-2-carbomethoxyaminobenzimidazole;
5(6)-pyrimidin-2-ylsulfinyl)-2-carbomethoxyaminobenzimidazole;
5(6)-(thien-2-ylthio)-2-carbomethoxyaminobenzimidazole; and
5(6)-(pyrid-4-ylthio)-2-carbomethoxyaminobenzimidazole.

Other illustrative compounds falling within the scope of the present invention include, for example:

5(6)-pyrimidin-2-yloxy)-2-carbomethyoxyaminobenzimindazole:
5(6)-(thien-2-yloxy)-2-carbomethoxyaminobenzimidazole;
5(6)-(1-methylimidazol-2-yloxy)-2-carbomethoxyaminobenzimidazole;
5(6)-(pyrid-4-yloxy)-2-carbomethoxyaminobenzimidazole;
5(6)-(pyrazin-2-ylsulfinyl)-2-carbomethoxyaminobenzimidazole;
5(6)-(pyrazin-2-yloxy)-2-carbomethoxyaminobenzimidazole;
5(6)-oxiranylthio-2-carbomethoxyaminobenzimidazole;
5(6)-oxiranylsulfinyl-2-carbomethoxyaminobenzimidazole;
5(6)-(tetrahydrothien-2-ylthio)-2-carbomethoxyaminobenzimidazole;
5(6)-(1-oxo-tetrahydrothien-2-ylthio)-2-carbomethoxyaminobenzimidazole;
5(6)-(tetrahydropyran-2-ylthio)-2-carbomethoxyaminobenzimidazole;
5(6)-(tetrahydropyran-2-ylsulfinyl)-2-carbomethoxyaminobenzimidazole;
5(6)-(benzothiazol-2-ylthio)-2-carbomethoxyaminobenzimidazole;
5(6)-tetrahydrothien-2-ylsulfinyl)-2-carbomethoxyaminobenzimidazole;
5(6)-thien-3-ylthio)-2-carbomethoxyaminobenzimidazole;
5(6)-thien-3-ylsulfinyl)-2-carbomethoxyaminobenzimidazole;
5(6)-(4-methoxy-tetrahydropyran-2-ylsulfinyl)-2-carbomethoxyaminobenzimidazole;
5(6)-(4-methoxy-tetrahydropyran-2-yloxy)-2-carbomethoxyaminobenzimidazole;
5(6)-(1,3,5-trithian-2-yloxy)-2-carbomethoxyaminobenzimidazole;
5(6)-(1,3,5-trithian-2-ylthio)-2-carbomethoxyaminobenzimidazole;
5(6)-(1,3,5-trithian-2-ylsulfinyl)-2-carbomethoxyaminobenzimidazole;
5(6)-(1,3-dithiolan-2-yloxy)-2-carbomethoxyaminobenzimidazole;
5(6)-(1,3-dithiolan-2-ylthio)-2-carbomethoxyaminobenzimidazole;
5(6)-(1,3-dithiolan-2-ylsulfinyl)-2-carbomethoxyaminobenzimidazole;
5(6)-(1,4-dithian-2-ylthio)-2-carbomethoxyaminobenzimidazole;
5(6)-(1,4-dithian-2-ylsulfinyl)-2-carbomethoxyaminobenzimidazole;
5(6)-(1,4-dioxan-2-yloxy)-2-carbomethoxyaminobenzimidazole;
5(6)-(1,4-dioxan-2-ylthio)-2-carbomethoxyaminobenzimidazole;
5(6)-(1,4-dioxan-2-ylsulfinyl)-2-carbomethoxyaminobenzimidazole;
5(6)-(fur-2-ylthio)-2-carbomethoxyaminobenzimidazole;
5(6)-(fur-2-ylsulfinyl)-2-carbomethoxyaminobenzimidazole;
5(6)-(4-methoxy-tetrahydropyran-2-ylthio)-2-carbomethoxyaminobenzimidazole;
5(6)-(1,2,4-triazol-3-yloxy)-2-carbomethoxyaminobenzimidazole;
5(6)-(thiazol-2-ylthio)-2-carboethoxyaminobenzimidazole;
5(6)-(thiazol-2-ylsulfinyl)-2-carboethoxyaminobenzimidazole;
5(6)-(thiazol-2-yloxy)-2-carboethoxyaminobenzimidazole;
5(6)-(pyrid-2-ylthio)-2-carboethoxyaminobenzimidazole;
5(6)-(pyrid-2-ylsulfinyl)-2-carboethoxyaminobenzimidazole;
5(6)-(pyrid-2-yloxy)-2-carboethoxyaminobenzimidazole;
5(6)-(pyrimidin-2-ylthio)-2-carboethoxyaminobenzimidazole;
5(6)-(pyrimidin-2-ylsulfinyl)-2-carboethoxyaminobenzimidazole;
5(6)-(thien-2-ylthio)-2-carboethoxyaminobenzimidazole;
5(6)-(thien-2-ylsulfinyl)-2-carboethoxyaminobenzimidazole;
5(6)-(1-methylimidazol-2-ylthio)-2-carboethoxyaminobenzimidazole;
5(6)-(1-methylimidazol-2-ylsulfinyl)-2-carboethoxyaminobenzimidazole;
5(6-(pyrid-4-ylthio)-2-carboethoxyaminobenzimidazole;
5(6)-(pyrid-4-ylsulfinyl)-2-carboethoxyaminobenzimidazole;
5(6)-(pyrazin-2-ylthio)-2-carboethoxyaminobenzimidazole;

5(6)-(1,2,4-triazol-3-ylthio)-2-carboethox-
yaminobenzimidazole; and

5(6)-(1,2,4-triazol-3-ylsulfinyl)-2-carboethox-
yaminobenzimidazole.

5(6)-(thiazol-2-ylthio)-2-carbopropoxyaminoben-
zimidazole;

5(6)-(thiazol-2-ylsulfinyl)-2-carbopropox-
yaminobenzimidazole;

5(6)-(thiazol-2-yloxy)-2-carbopropoxyaminoben-
zimidazole;

5(6)-(pyrid-2-ylthio)-2-carbopropoxyaminoben-
zimidazole;

5(6)-(pyrid-2-ylsulfinyl)-2-carbopropoxyaminoben-
zimidazole;

5(6)-(pyrid-2-yloxy)-2-carbopropoxyaminoben-
zimidazole;

5(6)-(pyrimidin-2-ylthio)-2-carbopropox-
yaminobenzimidazole;

5(6)-(pyrimidin-2-ylsulfinyl)-2-carbopropox-
yaminobenzimidazole;

5(6)-(thien-2-ylthio)-2-carbopropoxyaminoben-
zimidazole;

5(6)-(thien-2-ylsulfinyl)-2-carbopropoxyaminoben-
zimidazole;

5(6)-(1-methylimidazol-2-ylthio)-2-carbopropox-
yaminobenzimidazole;

5(6)-(1-methylimidazol-2-ylsulfinyl)-2-carbo-
propoxyaminobenzimidazole;

5(6)-(pyrid-4-ylthio)-2-carbopropoxyaminoben-
zimidazole;

5(6)-(pyrid-4-ylsulfinyl)-2-carbopropoxyaminoben-
zimidazole;

5(6)-(pyrazin-2-ylthio)-2-carbopropoxyaminoben-
zimidazole;

5(6)-(1,2,4,-triazol-3-ylthio)-2-carbopropox-
yaminobenzimidazole;

5(6)-(1,2,4-triazol-3-ylsulfinyl)-2-carbopropox-
yaminobenzimidazole;

5(6)-(thiazol-2-ylthio)-2-carbobutoxyaminoben-
zimidazole;

5(6)-(thiazol-2-ylsulfinyl)-2-carbobutoxyaminoben-
zimidazole;

5(6)-(thiazol-2-yloxy)-2-carbobutoxyaminoben-
zimidazole;

5(6)-(pyrid-2-ylthio)-2-carbobutoxyaminoben-
zimidazole;

5(6)-(pyrid-2-ylsulfinyl)-2-carbobutoxyaminoben-
zimidazole;

5(6)-(pyrid-2-yloxy)-2-carbobutoxyaminoben-
zimidazole;

5(6)-(pyrimidin-2-ylthio)-2-carbobutoxyaminoben-
zimidazole;

5(6)-(pyrimidin-2-ylsulfinyl)-2-carbobutox-
yaminobenzimidazole;

5(6)-(thien-2-ylthio)-2-carbobutoxyaminoben-
zimidazole;

5(6)-(thien-2-ylsulfinyl)-2-carbobutoxyaminoben-
zimidazole;

5(6)-(1-methylimidazol-2-ylthio)-2-carbobutox-
yaminobenzimidazole;

5(6)-(1-methylimidazol-2-ylsulfinyl)-2-carbobutox-
yaminobenzimidazole;

5(6)-(pyrid-4-ylthio)-2-carbobutoxyaminoben-
zimidazole;

5(6)-(pyrid-4-ylsulfinyl)-2-carbobutoxyaminoben-
zimidezole;

5(6)-(pyrazin-2-ylthio)-2-carbobutoxyaminoben-
zimidazole;

5(6)-(1,2,4-triazol-3-ylthio)-2-carbobutox-
yaminobenzimidazole; and

5(6)-(1,2,4-triazol-3-ylsulfinyl)-2-carbobutox-
yaminobenzimidazole.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

PREPARATION 1

175 G. of S-methyl isothiouronium sulfate in one liter of water is cooled to 0°C and 162.5 g. of methylchloroformate added, followed by the addition of a solution of 250 g. potassium hydroxide in 750 ml. water at 0° to 5°C. The crude product is extracted into benzene, the benzene dried and evaporated, and the residue recrystallized from methanol. 1,3-bis(methoxycarbonyl)-S-methyl isothiourea is thus obtained.

In a similar manner, substituting ethylchloroformate, propylchloroformate and butylchloroformate for the methylchloroformate, 1,3-bis(ethoxycarbonyl)-S-methyl isothiourea, 1,3-bis(propoxycarbonyl)-S-methyl isothiourea, and 1,3-bis(butoxycarbonyl)-S-methyl isothiourea are, respectively, prepared.

EXAMPLE I

3 G. of 1-acetamido-4-hydroxy-2-nitrobenzene is added to a solution of 0.62 g. of sodium hydroxide in 125 ml. of methanol under nitrogen. The mixture is stirred for ½ hour and the solvent evaporated. 2.5 G. of 2-bromothiazole and 100 ml. of dimethylformamide are added to the residue and the mixture heated at 135°C. for 16 hours. The solvent is evaporated, the residue is extracted with dichloromethane and the organic layers dried over anhydrous sodium sulfate. The solvent is evaporated and the residue recrystallized from aqueous methanol to yield 1-acetamido-2-nitro-4-(thiazol-2-yloxy)benzene.

2 G. of 1-acetamido-2-nitro-4-(thiazol-2-yloxy)benzene is added to a solution of 0.5 g. potassium hydroxide in 50 ml. methanol and the solution stirred for 1 hour. The solution is evaporated to a low volume and water is added to precipitate 1-amino-2-nitro-4-(thiazol-2-yloxy)benzene.

1.7 G. of the latter compound is dissolved in 100 ml. methanol and 0.5 g. of 5% palladium on charcoal is added. The mixture is hydrogenated under ambient conditions. After cessation of hydrogen uptake the mixture is filtered and the solvent evaporated from the filtrate to yield 1,2-diamino-4-(thiazol-2-yloxy)benzene as a brown oil.

1.5 G. of 1,2-diamino-4-(thiazol-2-yloxy)benzene 1.6 g. of 1,3-bis(methoxycarbonyl)-S-methyl-isothiourea and 0.5 g. acetic acid are added to a mixture of 75 ml. ethanol and 75 ml. water. The mixture is heated to reflux for three hours, then cooled. The precipitated solid is collected and recrystallized from methanol to yield 5(6)-(thiazol-2-yloxy)-2-carbomethox-yaminobenzimidazole.

EXAMPLE II

4 G. of 1-acetamido-4-hydroxy-2-nitrobenzene is added to a solution of 0.82 g. of sodium hydroxide in 100 ml. of methanol under nitrogen. The mixture is stirred for one-half hour and the solvent evaporated.

3.5 G. of 2-bromopyridine and 100 ml. of dimethylformamide are added to the residue and the mixture heated at 135°C. for 16 hours. The solvent is evaporated, the residue remaining is extracted with dichloromethane and the organic layers dried over anhydrous sodium sulfate. The solvent is evaporated and the residue recrystallized from aqueous methanol to yield 1-acetamido-2-nitro-4-(pyrid-2-yloxy)benzene.

2 G. of this latter compound is added to a mixture of 10 ml. of 5 N sodium hydroxide solution and 60 ml. methanol. The mixture is heated for 15 minutes, then diluted to 500 ml. with water. The mixture is extracted with dichloromethane and the organic layers are dried over anhydrous sodium sulfate. Evaporation of the organic layers affords 1-amino-2-nitro-4-(pyrid-2-yloxy)benzene.

1.4 G. of this latter compound is dissolved in 30 ml. methanol, and 0.4 g. of 5% palladium on charcoal is added. The mixture is hydrogenated under ambient conditions. After cessation of hydrogen uptake, the mixture is filtered and the solvent is evaporated from the filtrate to afford 1,2-diamino-4-(pyrid-2-yloxy)benzene.

1 G. of this latter compound and 0.65 g. of 1,3-bis-(methoxycarbonyl)-S-methyl isothiourea are added to a mixture of 5 ml. ethanol and 5 ml. water. The mixture is heated to reflux for 3 hours, then cooled. The precipitated solid is collected and recrystallized from methanol to yield 5(6)-(pyrid-2-yloxy)-2-carbomethoxyaminobenzimidazole.

EXAMPLE III

To a solution of 2.37 g. of 1-acetamido-2-nitro-4-thiocyanatobenzene in 10 ml. dimethylformamide, there is added under nitrogen at less than 30°C., 0.38 g. of sodium borohydrode. The mixture is stirred at 20°-30°C. for 1 hour, then 3.2 ml. of 2-bromothiazole is added. The mixture is heated to 130°-135°C. for 1 hour, then cooled and diluted with water. The crude product is filtered off and recrystallized from methanol yielding 1-acetamido-2-nitro-4-(thiazol-2-ylthio)benzene.

2.2 G. of this latter compound is treated on the steam bath for 15 minutes with 5 ml. 5N sodium hydroxide solution and 15 ml. methanol. The mixture is diluted with water and cooled, yielding 1-amino-2-nitro-4-(thiazol-2-ylthio)-benzene.

1.8 G. of 1-amino-2-nitro-4-(thiazol-2-ylthio)benzene in 5 ml. concentrated hydrochloric acid is treated with a solution of 3 g. stannous chloride in 5 ml. concentrated hydrochloric acid. The mixture is heated on the steam bath for 15 minutes and the resulting colorless solution cooled well. The white precipitate is filtered off and washed with 10 ml. 6N hydrochloric acid, then treated with potassium bicarbonate solution. The mixture is extracted with chloroform and the extract dried and evaporated. This affords 1,2-diamino-4-(thiazol-2-ylthio)benzene.

A mixture of 0.8 g. of 1,2-diamino-4-(thiazol-2-ylthio)-benzene, 0.8 g. 1,3-bis(methoxycarbonyl)-S-methyl-isothiourea and 0.24 ml. acetic acid in 10 ml. ethanol and 10 ml. water, is refluxed for 4 hours. The cooled mixture is filtered and the product recrystallized from methanol-chloroform yielding 5(6)-(thiazol-2-ylthio)-2-carbomethoxyaminobenzimidazole.

A solution of 0.92 g. of 5(6)-(thiazol-2-ylthio)-2-carbomethoxyaminobenzimidazole in 30 ml. acetic acid and 30 ml. chloroform is cooled to −20°C. and treated at −20°C. to −15°C. with a solution of 0.61 g. 85% m-chloroperbenzoic acid in 10 ml. chloroform. The mixture is allowed to warm slowly to room temperature, dried for five hours then stripped under vacuum at room temperature. The residue is treated with sodium bicarbonate solution, filtered, and The product recrystallized from methanol-chloroform affording 5(6)-(thiazol-2-ylsulfinyl)-2-carbomethoxyaminobenzimidazole.

EXAMPLE IV

A solution of 5.85 g. of 1-acetamido-2-nitro-4-thiocyanatobenzene in 20 ml. dimethylformamide is cooled, under nitrogen, to about 0°C. and 1.14 g. of sodium borohydride is added. The exothermic reaction is controlled to less than about 30°C., then the mixture is stirred for 1 hour at 20°-30°C. 6 Ml. of 2-bromopyridine is added and the mixture warmed slowly to about 110°C. and kept at that temperature for 1 hour. The mixture is cooled, diluted with water, and filtered. The crude product is recrystallized from aqueous methanol, yielding 1-amino-2-nitro-4-(pyrid-2-ylthio)benzene.

2.3 G. of 1-amino-2-nitro-4-(pyrid-2-ylthio)benzene in 12 ml. concentrated hydrochloric acid is treated with 12 g. of stannous chloride on the steam bath for 15 minutes. The cooled solution is treated with an excess of potassium bicarbonate and extracted with chloroform and filtered. The chloroform layer is separated, dried and evaporated to yield 1,2-diamino-4-(pyrid-2-ylthio)benzene.

A mixture of 1.75 g. of 1,2-diamino-4-(pyrid-2-ylthio)-benzene, 1.75 g. 1,3 -bis(methoxycarbonyl)-S-methylisothiourea and 0.6 ml. acetic acid in 20 ml. ethanol and 20 ml. water is refluxed for 2 hours, cooled and filtered. 5(6)-(pyrid-2-ylthio)-2-carbomethoxyaminobenzimidazole is thus obtained and may be recrystallized from methanolchloroform.

The 5(6)-(pyrid-2-ylthio)-2-carbomethoxyaminobenzimidazole is treated in accordance with the last paragraph of Example III to afford 5(6)-(pyrid-2-ylsulfinyl)-2-carbomethoxyaminobenzimidazole.

EXAMPLE V

A solution of 9.6 g. of 1-acetamido-2-nitro-4-thiocyanatobenzene in 60 ml. dimethylformamide is treated, under nitrogen, with 1.52 g. sodium borohydride at less than 25°C. The mixture is stirred for 1 hour at 20°-25°C., then 15 ml. of acetone is added and stirring continued for 2 hours. 2.5 G. of 57% sodium hydride in oil suspension is added at 20°-30°C., followed by 11.7 g. of 4-bromopyridine hydrochloride. The mixture is warmed slowly and kept at 120°-130°C. for several hours, then cooled and diluted with water, and extracted with chloroform. The chloroform solution is treated with charcoal, stripped and the residue recrystallized from methanol and washed with pentene affording 1-acetamido-2-nitro-4-(pyrid-4-ylthio)benzene.

3.15 G. of the latter compound is treated on the steam bath with 6 ml. 5N sodium hydroxide solution and 12 ml. methanol for 15 minutes. The mixture is diluted with water, cooled and filtered, yielding 1-amino-2-nitro-4-(pyrid-4-ylthio)benzene.

2.5 G. of the latter compound treated with 13 ml. concentrated hydrochloric acid and 13 g. stannous chloride on the steam bath for 15 minutes. The mixture is cooled, treated with potassium bicarbonate and extracted with chloroform. The dried chloroform extract, separated after filtration, is stripped yielding 1,2-diamino-4-(pyrid-4-ylthio)benzene.

A mixture of 2.1 g. of the latter compound, 2.2 g. 1,3-bis(methoxycarbonyl)-S-methyl-isothiourea and 1 ml. acetic acid in 35 ml. ethanol and 35 ml. water is refluxed for 3 hours. The mixture is cooled and filtered yielding 5(6)-(pyrid-4-ylthio)-2-carbomethoxyaminobenzimidazole which may be recrystallized from methanol-chloroform.

A solution of 1.2 g. of the latter compound in 75 ml. acetic acid and 75 ml. chloroform is cooled to −20°C. and a solution of 0.81 g. m-chloroperbenzoic acid in 15 ml. chloroform is added at −20° to −15°C. The mixture is allowed to warm slowly to 20°C, then stirred at 20°-25°C. for 5 hours, and stripped under vacuum. The residue is treated with sodium bicarbonate solution and filtered affording 5(6)-(pyrid-4-ylsulfinyl)-2-carbomethoxyaminobenzimidazole which may be recrystallized from methanol-chloroform.

EXAMPLE VI

A solution of 9.6 g. 1-acetamido-2-nitro-4-thiocyanatobenzene in 60 ml. dimethylformamide is treated under nitrogen with 1.52 g. of sodium borohydride, the exothermic reaction being controlled so that the temperature does not exceed 30°C. After stirring the mixture at 20°-25°C. for 1 hour, 15 ml. of acetone is added, then, after 2 hours, 9.1 g. of 2-chloropyrazine is added. The mixture is warmed slowly and kept at 100°-110°C. for 3 hours, cooled and diluted with water. The product is filtered off and washed with water, pentane and recrystallized from methanol affording 1-acetamido-2-nitro-4-(pyrazin-2-ylthio)benzene.

7.9 G. of the latter compound is treated on the steam bath for 15 minutes with a mixture of 16 ml. 5N sodium hydroxide and 16 ml. methanol. The mixture is diluted with water, cooled and filtered, yielding 1-amino-2-nitro-4-(pyrazin-2-ylthio)benzene.

A mixture of 6.4 g. of the latter compound, 6.4 g. iron powder, 3.2 g. ferrous sulfate in 480 ml. methanol and 120 ml. water is refluxed for 4 hours, filtered and the filtrate concentrated to dryness under vacuum. The residual 1,2-diamino-4-(pyrazin-2-ylthio)benzene is treated with 2.8 g. 1,3-bis(methoxycarbonyl)-S-methyl-isothiourea and 1 ml. acetic acid in 50 ml. ethanol and 50 ml. water at reflux for 5 hours. The mixture is cooled and filtered yielding 5(6)-(pyrazin-2-ylthio)-2-carbomethoxyaminobenzimidazole which may be recrystallized from methanol-chloroform.

A solution of 1.2 g. of the latter compound in 75 ml. chloroform and 75 ml. acetic acid is treated at −20° to −15°C. with a solution of 0.82 g. m-chloroperbenzoic acid. The mixture is allowed to warm slowly to room temperature, left for about 5 hours at 20° − 25°C, then stripped under vacuum. The residue is treated with sodium bicarbonate solution yielding -5(6)-(pyrazin-2-ylsulfinyl)-2-carbomethoxyaminobenzimidzole which may be filtered off and recrystallized from methanol-chloroform.

EXAMPLE VII

A mixture of 3.5 g. of 2-amino-4-chloro-1-nitrobenzene, 5.5 g. of potassium carbonate, and 4.5 g. of 2-mercaptopyrimidine in 25 ml. dimethylformamide is heated overnight under nitrogen at 105°-110°C. The mixture is cooled, diluted with water and the product filtered off. Recrystallization from methanol yields 2-amino-1-nitro-4-)pyrimidin-2-ylthio)benzene.

3.5 G. of 2-amino-1-nitro-4-(pyrimidin-2-ylthio)benzene is treated with 16 g. stannous chloride in 16 ml. concentrated hydrochloric acid on the steam bath for 30 minutes. The mixture is cooled, treated with an excess of potassium bicarbonate, chloroform, and filtered. The chloroform layer is dried and stripped yielding 1,2-diamino-4-(pyrimidin-2-ylthio)benzene which may be recrystallized from benzene.

A mixture of 0.7 g. of 1,2-diamino-4-(pyrimidin-2-ylthio)benzene, 0.7 g. 1,3-bis(methoxycarbonyl)-S-methyl-isothiourea and 0.25 ml. acetic acid in 10 ml. ethanol and 10 ml. water is refluxed for 2 hours. The cooled mixture is filtered and the product recrystallized from aqueous acetic acid affording 5(6)-(pyrimidin-2-ylthio)-2-carbomethoxyaminobenzimidazole.

0.28 G. of 5(6)-(pyrimidin-2-ylthio)-2-carbomethoxyaminobenzimidazole in 50 ml. acetic acid and 50 ml. chloroform is treated with 0.195 g. m-chloroperbenzoic acid according to the procedure in the last paragraph of Example III to yield, after recrystallization from methanol-chloroform, 5(6)-(pyrimidin-2-ylsulfinyl)-2-carbomethoxyaminobenzimidazole.

EXAMPLE VIII

14 G. of 2-(2,4-dinitrophenylthio)thiophene is treated, under nitrogen, with a refluxing solution of 5.6 g. potassium hydroxide in 275 ml. methanol for 15 minutes. The solution is then stripped under vacuum, 200 ml. of ice water is added, and filtered. The filtrate is concentrated under vacuum at less than 40°C. to dryness. 3.5 G. of 2-amino-4-chloro-1-nitrobenzene and 25 ml. dimethylformamide are added. The mixture is kept at 120°-130°C., under nitrogen, for 2 hours, cooled, diluted with water and extracted with chloroform. The chloroform extract is stripped and the residue recrystallized from methanol, with a charcoal treatment, to yield 2-amino-1-nitro-4-(thien-2-ylthio)benzene.

3.3 G. of 2-amino-1-nitro-4-(thien-2-ylthio)benzene is treated with 16 g. stannous chloride in 16 ml. concentrated hydrochloric acid on the steam bath for 5 minutes. The mixture is cooled, decanted and the gummy residue washed with 16 ml. 6N hydrochloric acid. The residue is dissolved in water, and treated with potassium bicarbonate solution and chloroform. The chloroform is dried and stripped yielding 1,2-diamino-4-(thien-2-ylthio)benzene.

2.0 G. of the latter compound, 2.0 g. 1,3-bis(carbomethoxy)-S-methyl-isothiourea and 0.7 ml. acetic acid in 25 ml. ethanol and 25 ml. water are refluxed for 3 hours. The mixture is cooled, filtered and the resulting 5(6)-(thien-2-ylthio)-2-carbomethoxyaminobenzimidazole recrystallized from methanol-chloroform.

0.91 G. of the latter compound is treated with 0.61 g. m-chloroperbenzoic acid in accordance with the procedure of the last paragraph of Example III to afford 5(6)-(thien-2-ylsulfinyl)-2-carbomethoxyaminobenzimidazole.

EXAMPLE IX

A mixture of 2.5 G. of 2-amino-4-chloro-1-nitrobenzene, 3.4 g. of 1-methyl-2-mercapto-imidazole and 4.2 g. potassium carbonate in 20 ml. dimethylformamide is heated overnight at 110°-120°C., then cooled, and poured into water. The product is filtered off and recrystallized from aqueous methanol to give 2-amino-4-(1-methylimidazol-2-ylthio)-1-nitrobenzene.

2.8 G. of the latter compound is treated with 13 g. stannous chloride in 13 ml. concentrated hydrochloric acid on the steam bath for 10 minutes. The cooled mixture is treated with potassium bicarbonate and chloroform, then filtered and the chloroform layer reheated and evaporated to yield 1,2-diamino-4-(1-methylimidazol-2-ylthio)benzene.

A mixture of 2.5 g. of the latter compound and 2.5 g. of 1,3-bis(methoxycarbonyl)-S-methyl isothiourea and 0.8 ml. acetic acid in 25 ml. ethanol and 25 ml. water is refluxed for 3 hours. The cooled mixture is filtered and the product recrystallized from methanol yielding 5(6)-(1-methylimidazol-2-ylthio)-2-carbomethoxyaminobenzimidazole.

0.91 G. of the latter compound in 75 ml. acetic acid and 75 ml. chloroform is treated with 0.61 g. m-chloroperbenzoic acid in accordance with the procedure of the last paragraph of Example III. The product is recrystallized from methanol-chloroform to yield 5(6)-(1-methylimidazol-2-ylsulfinyl)-2-carbomethoxyaminobenzimidazole.

EXAMPLE X

A mixture of 3.5 g. 2-amino-4-chloro-1-nitrobenzene, 5.5 g. of potassium carbonate, 4.0 g. of 3-mercapto-1,2,4-triazole in 30 ml. dimethylformamide is heated under nitrogen for 4 hours at 130°–140°C. The mixture is cooled, diluted with water and the pH adjusted to about 6. The crude product is filtered off and recrystallized from methanol, yielding 2-amino-1-nitro-4-(1,2,4-triazol-3-ylthio)benzene.

A mixture of 3.2 g. 2-amino-1-nitro-4-(1,2,4-triazol-3-ylthio)benzene, 3.2 g. of iron powder, 1.6 g. ferrous sulfate in 240 ml. methanol and 60 ml. water is refluxed for 6 hours (with one additional portion of iron being added after 3 hours. The mixture is cooled, filtered and the filtrate stripped under vacuum to yield 1,2-diamino-4-(1,2,4-triazol-3-ylthio)benzene.

A mixture of 2.6 g. of 1,2-diamino-4-(1,2,4-triazol-3-ylthio)benzene, 2.75 g. of 1,3-bis(methoxycarbonyl)-S-methyl-isothiourea and 1 ml. of acetic acid in 50 ml. ethanol and 50 ml. water is refluxed for 4 hours. The cooled mixture is filtered and the solid product is dissolved in 15 ml. of 2 N hydrochloric acid. The solution is filtered then the pH adjusted to about 7 and the 5(6)-(1,2,4-triazol-3-ylthio)-2-carbomethoxyaminobenzimidazole filtered off and washed with water, then methanol.

1.16 g. of the latter compound is treated in 75 ml. acetic acid and 75 ml. chloroform at −20°C. with 0.81 g. m-chloroperbenzoic acid in accordance with the last paragraph of Example III to yield 5(6)-(1,2,4-triazol-3-ylsulfinyl)-2-carbomethoxyaminobenzimidazole. This is purified by precipitation with ammonia from a solution thereof in 40 ml. 1N hydrochloric acid, filtered off and washed with water and methanol.

EXAMPLE XI

A solution of 2.0 g. 2-mercaptoimidazole in 25 ml. dimethylformamide is treated with 0.85 g. of 57% sodium hydride (in oil suspension). 3.0 G. of 2-amino-4-chloro-1-nitrobenzene is added and the mixture heated overnight at 150°–155°C. The mixture is diluted with water, filtered and the crude product washed with chloroform, recrystallized from aqueous methanol to yield 2-amino-4-(imidazol-2-ylthio)-1-nitrobenzene.

A mixture of 2.6 g. of 2-amino-4-(imidazol-2-ylthio)-1-nitrobenzene, 2.6 g. of iron powder and 1.3 g. ferrous sulfate in 200 ml. methanol and 50 ml. water is refluxed for 2 hours. An additional 2.6 g. of iron is added and refluxing continued for 2 hours. The mixture is filtered and the filtrate stripped to yield 1,2-diamino-4-(imidazol-2-ylthio)benzene.

A mixture of 2.7 g. of 1,2-diamino-4-(imidazol-2-ylthio)benzene, 2.3 g. 1,3-bis(methoxycarbonyl)-S-methylisothiourea and 0.8 ml. acetic acid in 25 ml. ethanol and 25 ml. water is refluxed for 4 hours. The cooled mixture is filtered and the product recrystallized from methanol-chloroform yielding 5(6)-(imidazol-2-ylthio)-2-carbomethoxyaminobenzimidazole.

0.58 G. of the latter compound is treated in 100 ml. chloroform and 20 ml. acetic acid with 0.41 g. m-chloroperbenzoic acid at −20°C. in accordance with the last paragraph of Example III to yield 5(6)-(imidazol-2-ylsulfinyl)-2-carbomethoxyaminobenzimidazole, which can be recrystallized from methanol-chloroform.

EXAMPLE XII

The procedure of Example I is repeated except 2-bromopyrimidine, 2-bromopyridazine, 4-bromopyridine, 2-chloropyrazine, 5-bromo-1-methyl-1,2,3-triazole, 5-chloro-3-methyl-1,2,4-thiadiazole, 2-bromo-1,3,4-thiadiazole, and 2-bromo-4-methyltetrazole are substituted for the 2-bromothiazole of Example I to afford, respectively:

5(6)-(pyrimidin-2-yloxy)-2-carbomethoxyaminobenzimidazole;

5(6)-(pyridazin-2-yloxy)-2-carbomethoxyaminobenzimidazole;

5(6)-(pyrid-4-yloxy)-2-carbomethoxyaminobenzimidazole;

5(6)-(pyrazin-2-yloxy)-2-carbomethoxyaminobenzimidazole;

5(6)-(1-methyl-1,2,3-triazol-5-yloxy)-2-carbomethoxyaminobenzimidazole;

5(6)-(3-methyl-1,2,4-thiadiazol-5-yloxy)-2-carbomethoxyaminobenzimidazole;

5(6)-(1,3,4-thiadiazol-2-yloxy)-2-carbomethoxyaminobenzimidazole; and

5(6)-(4-methyltetrazol-2-yloxy)-2-carbomethoxyaminobenzimidazole.

EXAMPLE XIII

The procedures of Examples I, II and XII are repeated except 1,3-bis(ethoxycarbonyl)-S-methyl isothiourea, 1,3-bis(propoxycarbonyl)-S-methyl isothiourea, or 1,3-bis-(butyoxycarbonyl)-S-methyl isothiourea is substituted for the 1,3-bis(methoxycarbonyl)-S-methyl isothiourea to afford the corresponding 5(6)-(heterocyclicoxy)-2-carbethoxyaminobenzimidazole, 5(6)-(heterocyclicoxy)-2-carbopropoxyaminobenzimidazole, and 5(6)-(heterocyclicoxy)-2-carbobutoxyaminobenzimidazole compounds.

EXAMPLE XIV

The procedures of Examples III–XI are repeated except 1,3-bis(ethoxycarbonyl)-S-methyl isothiourea, 1,3-bis(propoxycarbonyl)-S-methyl isothiourea, or 1,3-bis(butoxycarbonyl)-S-methyl isothiourea is substituted for the 1,3-bis(methoxycarbonyl)-S-methyl isothiourea to afford the corresponding 5(6)-heterocyclicthio-2-carbalkoxyaminobenzimidazole and 5(6)-heterocyclicsulfinyl-2-carbalkoxyaminobenzimidazole compounds where R (of the alkoxy portion of the 2-substituent) is either ethyl, propyl or butyl.

EXAMPLE XV

The halides listed in Example XII are substituted for the halide compounds of Examples III, IV, V and/or VI above to afford the following heterocyclicthio compounds:

5(6)-(pyrimidin-2-ylthio)-2-carbomethoxyaminobenzimidazole;
5(6)-(pyridazin-2-ylthio)-2-carbomethoxyaminobenzimidazole;
5(6)-(pyrid-4-ylthio)-2-carbomethoxyaminobenzimidazole;
5(6)-(pyrazin-2-ylthio)-2-carbomethoxyaminobenzimidazole;
5(6)-(1-methyl-1,2,3-triazol-5-ylthio)-2-carbomethoxyaminobenzimidazole;
5(6)-(3-methyl-1,2,4-thiadiazol-5-ylthio)-2-carbomethoxyaminobenzimidazole;
5(6)-(1,3,4-thiadiazol-5-ylthio)-2-carbomethoxyaminobenzimidazole; and
5(6)-(4-methyltetrazol-2-ylthio)-2-carbomethoxyaminobenzimidazole.

EXAMPLE XVI

The heterocyclicthio compounds of Example XV are treated with a peracid in accordance with the techniques described herein to afford the corresponding heterocyclicsulfinyl-2-carbomethoxyaminobenzimidazoles.

EXAMPLE XVII

Example I is repeated except 3-iodofuran, 2-iodothiophene, 3-bromothiophene, 5-bromoisothiazole, 3-chloro-5-phenyl-isoxazole and 2-chloro-1,3-4-thiadiazole are substituted for the 2-bromothiazole, and the reaction thereof with 1-acetamido-2-nitro-4-hydroxybenzene is conducted in the presence of copper oxide, to afford, respectively, 5(6)-(fur-3-yloxy)-2-carbomethoxyaminobenzimidazole, 5(6)-(thien-2-yloxy)-2-carbomethoxyaminobenzimidazole, 5(6)-(thien-3-yloxy)-2-carbomethoxyaminobenzimidazole, 5(6)-(isothiazol-5-yloxy)-2-carbomethoxyaminobenzimidazole, 5(6)-(5-phenyl-isoxazol-2-yloxy)-2-carbomethoxyaminobenzimidazole, and 5(6)-(1,3,4-thiadiazol-2-yloxy)-2-carbomethoxyaminobenzimidazole.

EXAMPLE XVIII

Example XI is repeated except 2-hydroxythiophene, 3-hydroxyisothiazole, 2-hydroxy-3,4-dimethylpyrrole, 3-hydroxy-1,2,5-thiadiazole, 2-mercaptooxazole are substituted for the 2-mercaptoimidazole to afford, respectively 5(6)-(thien-2yloxy)-2-carbomethoxyaminobenzimidazole; 5(6)-(isothiazol-3-yloxy)-2-carbomethoxyaminobenzimidazole; 5(6)-(3,4-dimethylpyrrol-2-yloxy)-2-carbomethoxyaminobenzimidazole; 5(6)-(1,2,5-thiadiazol-3-yloxy)-2-carbomethoxyaminobenzimidazole; and 5(6)-(oxazol-2-yloxy)-2-carbomethoxyaminobenzimidazole.

EXAMPLE XIX

A mixture of 5 g. of 2-nitro-5-chloroaniline, 7.5 g. of sodium sulfide monohydrate in 25 ml. of ethanol and 25 ml. of water is refluxed for 1 hour, diluted with water to about 150 ml. and filtered. The filtrate is treated with 2.5 ml. of acetic acid and 2-nitro-5-mercaptoaniline filtered off.

3.4 G. of 2-amino-4-mercapto-1-nitrobenzene is dissolved in 40 ml. of dimethylformamide under nitrogen and treated at 20°–25°C with 0.5 g. of 100% sodium hydride. After 1 hour, 2.8 g. of cuprous oxide and 4.0 g. of 3-bromothiophene are added. The mixture is heated in an oil bath for 5 hours at 140°–150°C, cooled, diluted with water, and extracted with chloroform. The chloroform solution is passed through a silica gel column and the eluate evaporated to yield 2-amino-4-(3-thienylthio)-1-nitrobenzene.

1.6 G. of 2-amino-4-(3-thienylthio)-1-nitrobenzene is treated with 1.6 g. of iron powder in a refluxing mixture of 1.6 ml. of water, 0.16 ml. of conc. hydrochloric acid and 100 ml. of toluene. After 3 hours when the reaction is complete, the iron residue is filtered off and the filtrate stripped under vacuum to afford 1,2-diamino-4-(3-thienylthio)-benzene.

1.5 G. of 1,2-diamino-4-(3-thienylthio)benzene is treated with 1.5 g. of 1,3-bis(methoxycarbonyl)-S-methyl isothiourea and 0.5 ml. of acetic acid in a refluxing mixture of 30 ml. of water and 30 ml. of ethanol. After 4 hours, the mixture is cooled and 5(6)-(3-thienylthio)-2-carbomethoxyaminobenzimidazole obtained by filtration. It may be recrystallized from methanol-chloroform.

0.61 G. of 5(6)-(3-thienylthio)-2-carbomethoxyaminobenzimidazole is treated in a mixture of 20 ml. of acetic acid and 100 ml. of chloroform at −20°C with a solution of 0.42 g. of metachloroperbenzoic acid. The mixture is allowed to warm slowly to room temperature, kept at room temperature for 1 hour, then evaporated under vacuum and the residue treated with dilute sodium bicarbonate solution. The crude product is filtered off and recrystallized from methanol-chloroform to afford 5(6)-(3-thienylsulfinyl)-2-carboxymethoxyaminobenzimidazole.

The above reaction sequence through 2-amino-4-mercapto-1-nitrobenzene provides an additional route by which certain of the compounds of this invention can be prepared.

In a similar manner, substituting 3-idofuran, 2-bromofuran, 3-chloro-5-phenyl-isoxazole, 5-bromoisothiazole and 2-chloro-1,3,4-thiadiazole for the 3-bromothiophene above, the following compounds, respectively, are prepared:

5(6)-(fur-3-ylthio)-2-carbomethoxyaminobenzimidazole and 5(6)-(fur-3-ylsulfinyl)-2-carbomethoxyaminobenzimidazole;
5(6)-(fur-2-ylthio)-2-carbomethoxyaminobenzimidazole and 5(6)-(fur-2-ylsulfinyl)-2-carbomethoxyaminobenzimidazole;
5(6)-(5-phenyl-isoxazol-3-ylthio)-2-carbomethoxyaminobenzimidazole and 5(6)-(5-phenyl-isoxazol-3-ylsulfinyl)-2-carbomethoxyaminobenzimidazole;
5(6)-(isothiazol-2-ylthio)-2-carbomethoxyaminobenzimidazole and 5(6)-(isothiazol-2-ylsulfinyl)-2-carbomethoxyaminobenzimidazole;
5(6)-(1,3,4-thiadiazol-2-ylthio)-2-carbomethoxyaminobenzimidazole and 5(6)-(1,3,4-thiadiazol-2-ylsulfinyl)-2-carbomethoxyaminobenzimidazole.

EXAMPLE XX

Example III is repeated except 1-amino-2-nitro-5-chlorobenzene is substituted for the 1-acetamido-2-nitro-4-thiocyanatobenzene, and 3-thiocyanatopyrrole is substituted for the 2-bromothiazole to afford 5(6)-(pyrrol-3-ylthio)-2-carbomethoxyaminobenzimidazole and 5(6)-(pyrrol-3-ylsulfinyl)-2-carbomethoxyaminobenzimidazole.

In certain of the Examples above, specific reaction sequences have been extended, in a general sense, to the preparation of other similar and related compounds. It should be understood, however, that with respect to any compound which has been prepared by the extension of a specific reaction sequence, it may be necessary or desirable to utilize solvents, reaction media, recrystallization media, reaction times or temperatures, etc., other than the ones given in the specific reaction sequence upon which such extension is based. Additionally, the specific reaction sequence or manner in which particular compounds are to be prepared will depend, inter alia, upon the availability of the necessary starting materials, or the ease in which the desired starting materials can be prepared, and the reactivity thereof. Reactivity can be enhanced, for example, by using materials, such as, for example, the copper oxide of Example XIX. These variations are deemed to be within the skill of those working in this art and will be apparent from a consideration of the particular reactants utilized and/or particular compound desired to be produced.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A compound selected from the group of compounds represented by the formula:

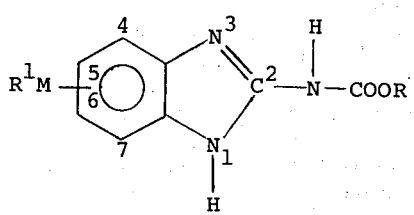

where R is a lower alkyl group having 1 to 4 carbon atoms; $R^1$ is selected from the group consisting of thiazolyl, pyridyl, imidazolyl, pyrimidinyl, thienyl, pyridazinyl, pyrazinyl, pyrrolyl, pyrazolyl, oxazolyl, furyl, isothiazolyl, isoxazolyl, thiadiazolyl, and triazolyl, and M is O, S, or $$\underset{O}{\overset{S}{\downarrow}}$$

the $R^1$ M-substitution being at the 5(6)-position; or a pharmaceutically acceptable salt thereof.

2. The compound of claim 1 wherein R is methyl.
3. The compound of claim 1 wherein M is O.
4. The compound of claim 1 wherein M is S.
5. The compound of claim 1 wherein M is $$\underset{O}{\overset{S}{\downarrow}}$$

6. The compound of claim 1 where $R^1$ is thiazol-2-yl.
7. The compound of claim 1 where $R^1$ is pyrid-2-yl.
8. The compound of claim 1 where $R^1$ is pyrimidin-2-yl.
9. The compound of claim 1 where $R^1$ is thien-2-yl.
10. The compound of claim 1 wherein said compound is 5(6)-(thiazol-2-ylthio)-2-carbomethoxyaminobenzimidazole.
11. The compound of claim 1 wherein said compound is 5(6)-(pyrid-2-ylthio)-2-carbomethoxyaminobenzimidazole.
12. The compound of claim 1 wherein said compound is 5(6)-(pyrid-2-ylsulfinyl)-2-carbomethoxyaminobenzimidazole.
13. The compound of claim 1 wherein said compound is 5(6)-(pyrid-2-yloxy)-2-carbomethoxyaminobenzimidazole.
14. The compound of claim 1 wherein said compound is 5(6)-(pyrimidin-2-ylsulfinyl)-2-carbomethoxyaminobenzimidazole.
15. The compound of claim 1 wherein said compound is 5(6)-(thien-2-ylthio)-2-carbomethoxyaminobenzimidazole.
16. The compound of claim 1 wherein said compound is 5(6)-(pyrid-4-ylthio)-2-carbomethoxyaminobenzimidazole.
17. The compound of claim 1 wherein said compound is 5(6)-(fur-2-ylsulfinyl)-2-carbomethoxyaminobenzimidazole.
18. The compound of claim 1 where $R^1$ is pyrid-4-yl.
19. The compound of claim 1 where $R^1$ is fur-2-yl.
20. The compound of claim 1 where $R^1$ is pyrazin-2-yl.
21. The compound of claim 1 wherein said compound is 5(6)-(pyrazin-2-ylsulfinyl)-2-carbomethoxyaminobenzimidazole.
22. The compound of claim 1 wherein said compound is 5(6)-(fur-2-ylthio)-2-carbomethoxyaminobenzimidazole.

* * * * *

PO-1050
(5/69)

UNITED STATES PATENT OFFICE
CERTIFICATE OF CORRECTION

Patent No. 3,935,209  Dated January 27, 1976

Inventor(s) COLIN C. BEARD et al

It is certified that error appears in the above-identified patent and that said Letters Patent are hereby corrected as shown below:

Column 1, line 4, immediately following the Title, insert -- REFERENCE TO PARENT APPLICATION This application is a continuation-in-part application of application Serial No. 340,581, filed March 12, 1973. --.

Column 11, lines 59-60, "-ylthio)-benzene" should read -- -ylthio)benzene --. Claim 1, in the fifth line below the structural formula, "triazolyl," should read -- triazolyl; --.

Signed and Sealed this

Twenty-first Day of September 1976

[SEAL]

Attest:

RUTH C. MASON
Attesting Officer

C. MARSHALL DANN
Commissioner of Patents and Trademarks